United States Patent
Bonnet

(10) Patent No.: US 6,206,853 B1
(45) Date of Patent: Mar. 27, 2001

(54) SELF-RETRACTING SYRINGE NEEDLE

(76) Inventor: Jean-Pierre Bonnet, 4, rue Roger Salengro, Ferrieres, 77164 (FR)

(*) Notice: Subject to any disclaimer, the term of this patent is extended or adjusted under 35 U.S.C. 154(b) by 0 days.

(21) Appl. No.: 09/445,368
(22) PCT Filed: Jun. 9, 1998
(86) PCT No.: PCT/FR98/01177
  § 371 Date: May 9, 2000
  § 102(e) Date: May 9, 2000
(87) PCT Pub. No.: WO98/56442
  PCT Pub. Date: Dec. 17, 1998

(30) Foreign Application Priority Data

Jun. 10, 1997 (FR) .................................................. 97/07185

(51) Int. Cl.⁷ .................................................. A61M 5/00
(52) U.S. Cl. .......................................... 604/110; 604/195
(58) Field of Search .................................... 604/110, 195, 604/263, 198, 192, 187

(56) References Cited

FOREIGN PATENT DOCUMENTS

| 685979 A5 | 11/1995 | (CH) . |
| 2680110 | 2/1993 | (FR) . |
| WO 91/13643 | 9/1991 | (WO) . |
| WO 92/09319 | 6/1992 | (WO) . |
| WO 93/00949 | 1/1993 | (WO) . |
| WO 95/23004 | 8/1995 | (WO) . |

Primary Examiner—John D. Yasko
(74) Attorney, Agent, or Firm—Perman & Green, LLP

(57) ABSTRACT

The invention concerns a self-retracting syringe needle comprising a body (1) supporting an injection needle, a plunger (4), a sheath (5) enclosing the body (1), a spring (6) arranged between the sheath (5) and the body (1), flexible pins (7) co-operating as limit stop with the body (1) to define a first position blocking the body (1) relative to the sheath (5) in a first direction. The syringe comprises a circlip (9) mounted around the body (1) in a position compressed between the sheath (5) and the body (1) in the first blocking position and in a released position in the second blocking position, the circlip (9) having at least one part (9a) with external contour of greater dimension than the sheath (5) internal dimension to block the body (1) in the sheath (5) when it is in the second blocking position, in the direction opposite to the first.

10 Claims, 5 Drawing Sheets

Figure 1:
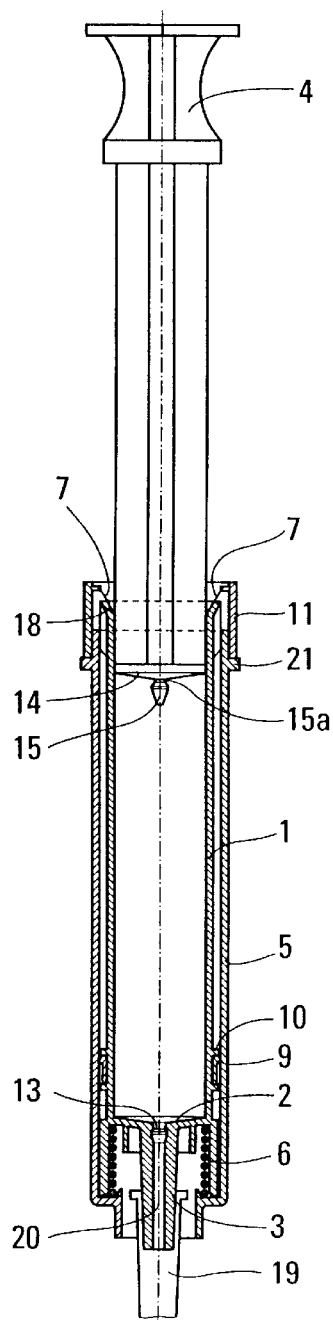

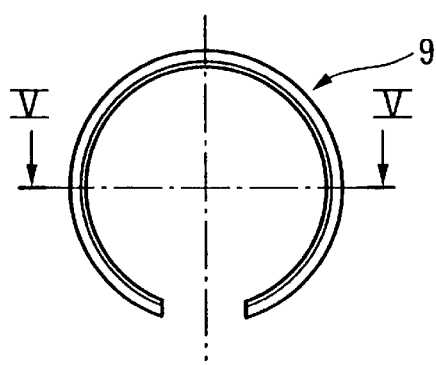
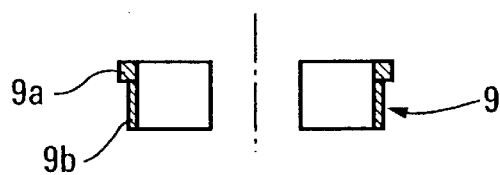
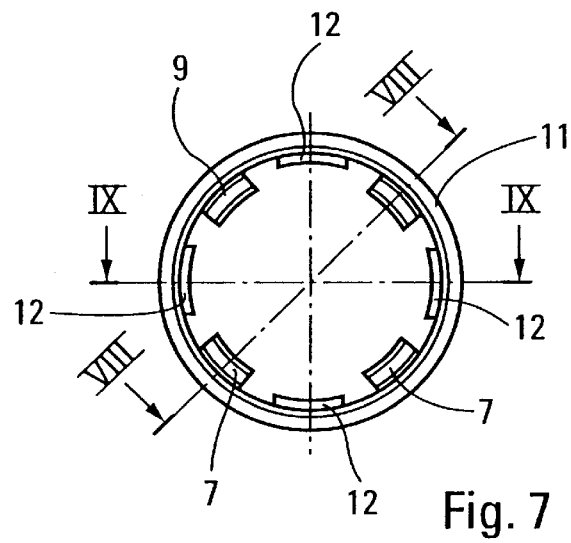
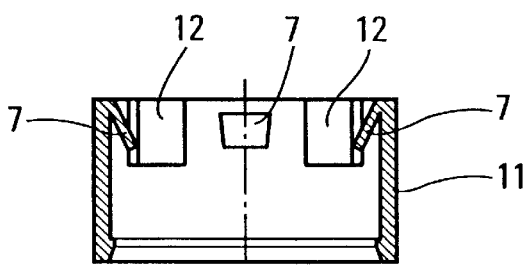
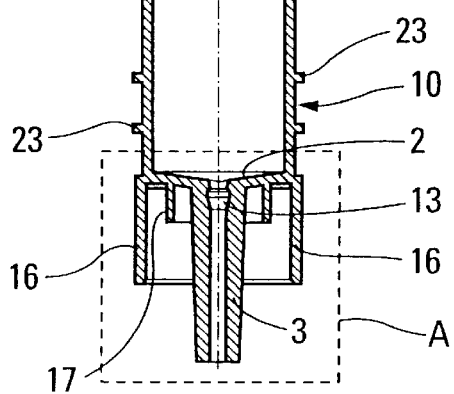
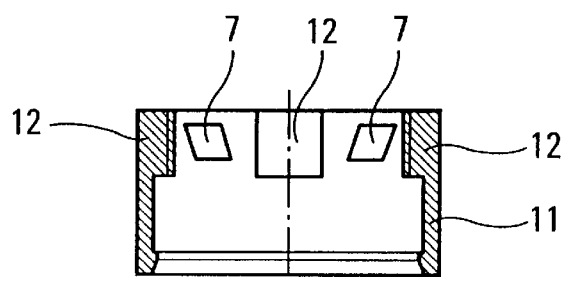

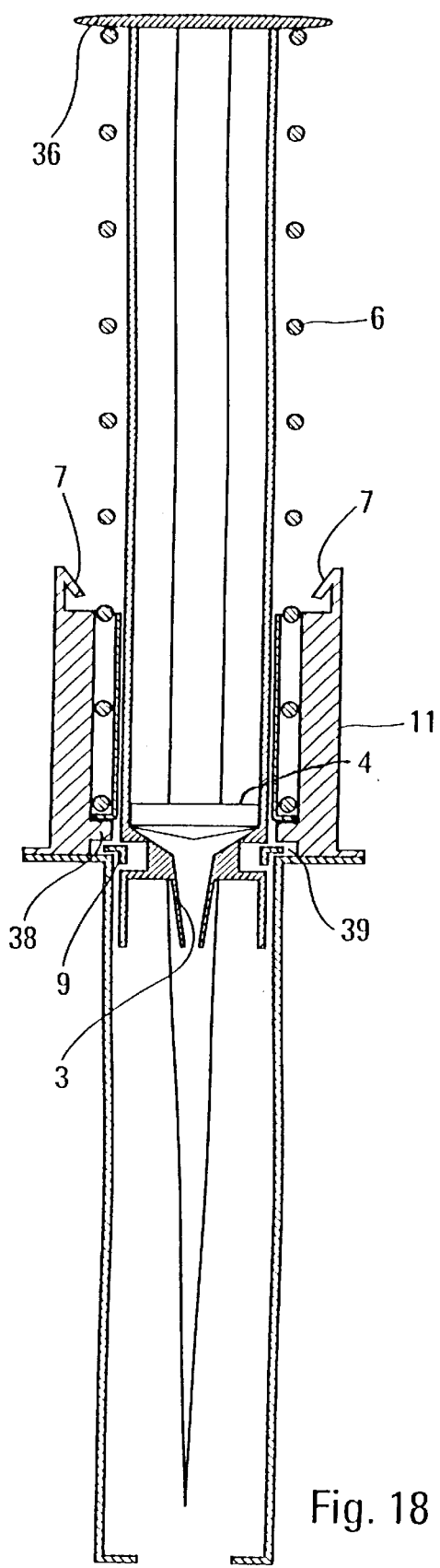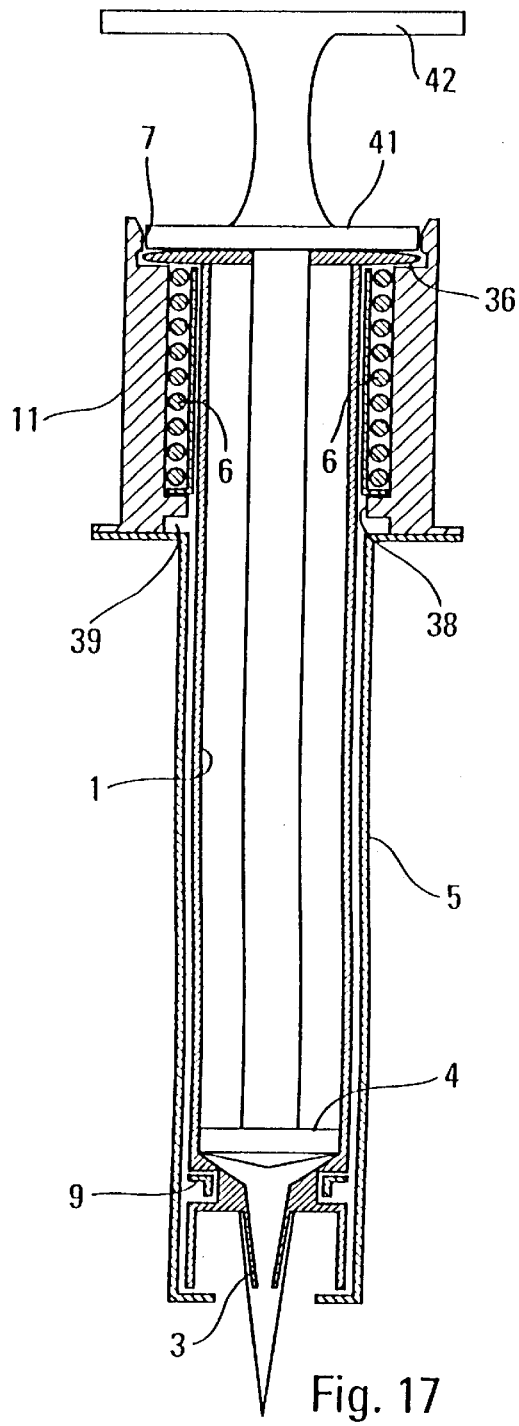
Fig. 18
Fig. 17

SELF-RETRACTING SYRINGE NEEDLE

The present invention concerns a syringe with a self-retracting needle.

It also concerns a circlip for preventing relative movement in translation of two bodies sliding one within the other.

Medical syringes are used to inject a substance, generally medication, into the body of a patient using a hollow needle.

So-called single-use syringes are now in general use, and are sold in a sterile condition in sealed packaging. The intention is that they should not be reused, with the aim of preventing any risk of accidental contamination of one patient by another. However, this widely used equipment does not protect medical personnel from accidental pricking and does not materially prevent reuse of the syringe if the user does not intentionally destroy it after use.

Document PCT/FR90/00572 describes a syringe with a self-retracting needle, comprising a body carrying injection-needle support means at one end, a piston mobile in said body, a sheath in which the body can slide, and a spring disposed between the sheath and the body. At least one first flexible lug is also provided, carried by the sheath and cooperating in abutment fashion with a first shoulder to define a first position of immobilization of the body relative to the sheath in a first direction, the spring being compressed and the needle being deployed from the sheath in this first position, and with a second shoulder to define a second position of immobilization in the same direction, the spring being at least partly relaxed and the needle being inside the sheath in this second position. The change from the first position to the second position is effected by cooperation of the piston with the flexible lug to release the lug from the first shoulder at the end of the travel of the piston and thereby, due to the effect of the spring, cause the body to be withdrawn into the sheath until it is immobilized in the second position.

The above syringe has at least one second flexible lug and at least one third shoulder, in respective opposite directions to the first flexible lug and to the two first shoulders, respectively on the sheath and on the wall of the body to immobilize the body in the sheath when it is in the second immobilizing position, in the direction opposite to the first direction.

However, the type of syringe well known in the art has the drawback that its flexible lugs can easily be broken when the user attempts to return the body to its first immobilizing position in the sheath with the aim of using the syringe again.

The flexible immobilizing lugs therefore do not guarantee single use of the syringe.

Document FR 2 680 110 describes a syringe having a body that can slide inside a sheath and is prevented from sliding inside the sheath by a circlip which lodges in two grooves which are aligned in the immobilizing position, one of the grooves being formed on the outside wall of the body of the syringe and the other groove being formed on the inside wall of the sheath.

This immobilizing system is complicated to manufacture because it requires grooves on the inside of the sheath and on the outside of the syringe body.

The object of the present invention is to propose a single-use syringe with a self-retracting needle preventing the user deploying the needle from the sheath again after using the syringe.

The syringe in accordance with the invention with a self-retracting needle comprises a body carrying injection needle support means at one end, a piston mobile in said body, a sheath inside which said body can slide, a spring disposed between the sheath and the body, at least one flexible lug cooperating abutment-fashion with a portion of the body to define a first position of immobilization of the body relative to the sheath in a first direction, the spring being compressed and the needle deployed from the sheath in this first position, and immobilizing means for immobilizing the body in the sheath in a second immobilizing position, the spring being at least partially relaxed and the needle being inside the sheath in this second position, the change from the first position to the second position being effected by cooperation of the piston with said flexible lug to release the lug from said portion of the body substantially at the end of the travel of the piston and thereby to cause the spring to retract the body into the sheath until it is immobilized in the second position.

According to the invention, the syringe is characterized in that the immobilizing means comprise a circlip mounted around said body in a compressed configuration between the sheath and the body in said first immobilizing position and in a relaxed position in said second immobilizing position, the sheath having at one end a sleeve part, the circlip having at least one part housed inside the sleeve part in said second immobilizing position between said end of the sheath and at least one shoulder of the sleeve part adapted to cooperate abutment-fashion with the circlip in said second immobilizing position to immobilize the body in the sheath in said first direction.

The circlip, which expands into the relaxed position, prevents reinsertion of the body into the sheath, which prevents deployment of the needle.

The abutting cooperation of the circlip with the end of the sheath immobilizes the body relative to the sheath in a way that is much more resistant to attempts to reinsert the body into the sheath than the flexible lugs used in syringes well known in the art, which form localized immobilizing points that are easily deformed or destroyed.

The part forming the sleeve around the sheath forms a housing for the circlip in the relaxed configuration so that the user has no access to the circlip and cannot attempt to return it to the compressed configuration in order to reinsert it into the sheath.

In a preferred version of the invention, the circlip has an L-shaped cross section and the leg of the L-shape is lodged between the sheath and the body in the second immobilizing position.

This prevents relative movement of the sheath and the syringe body not only in the longitudinal direction of the syringe but also in a transverse plane of the syringe.

Other features and advantages of the invention will become more apparent in the following description.

Figure 2:
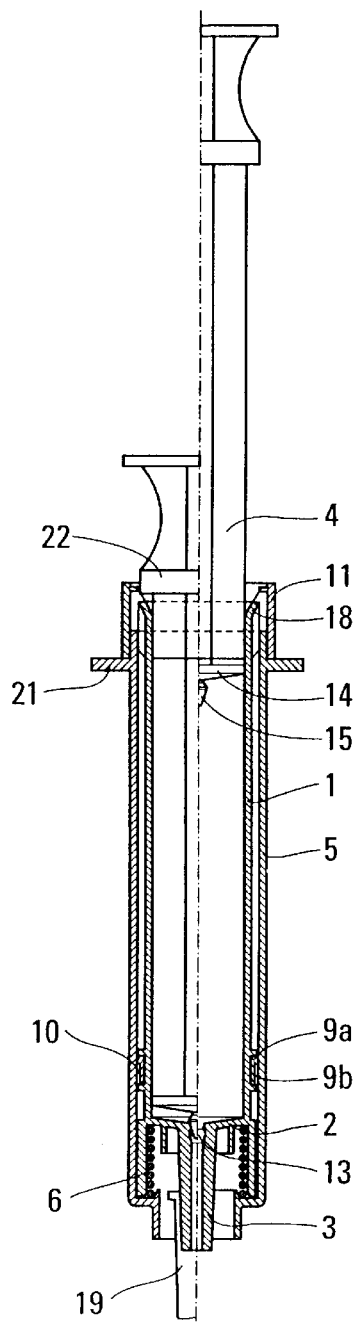
Figure 3:
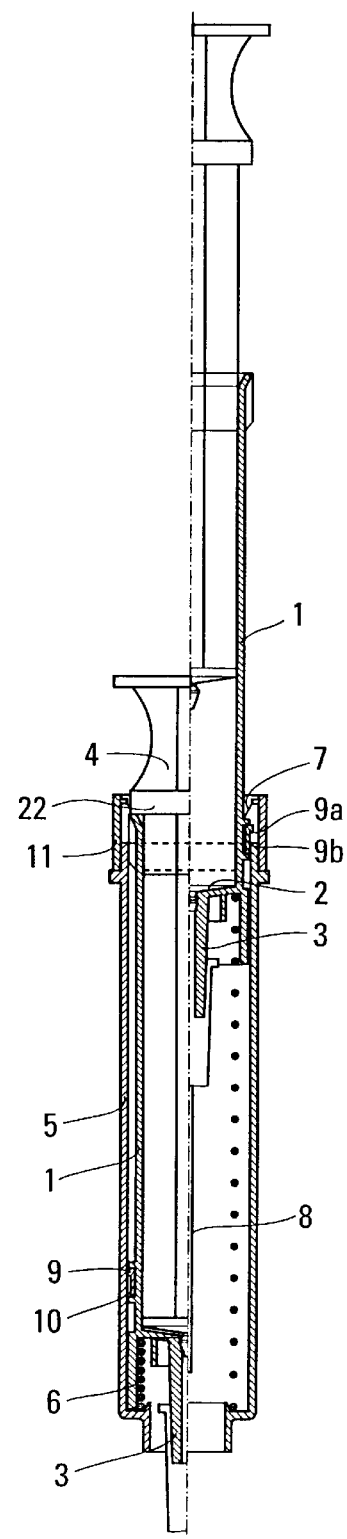
Figure 10:
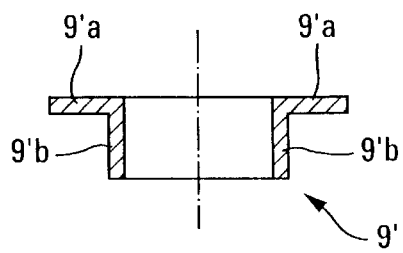
Figure 11:
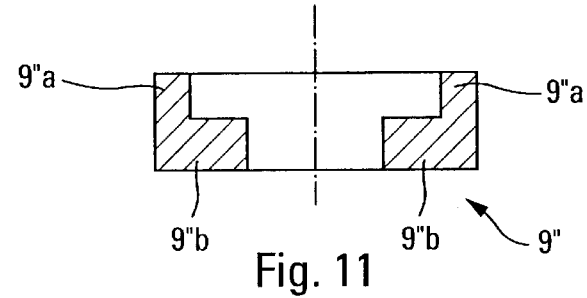
Figure 12:
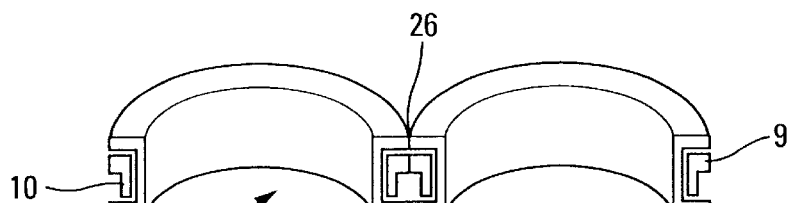
Figure 14:
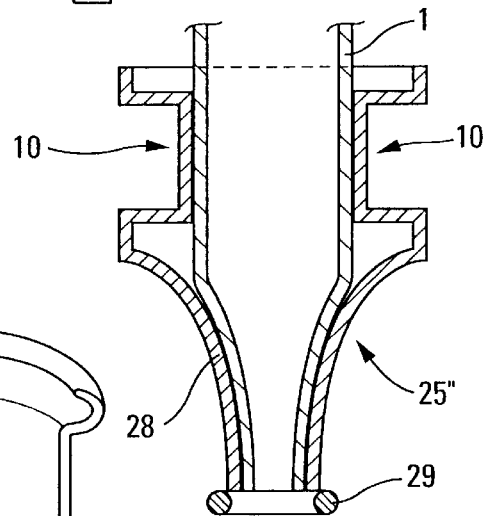
Figure 13:
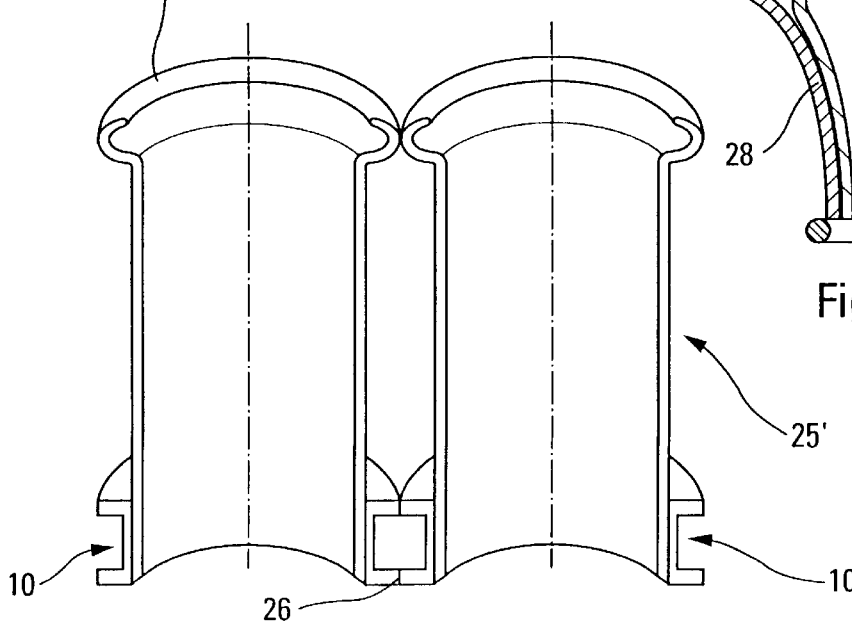
Figure 16:
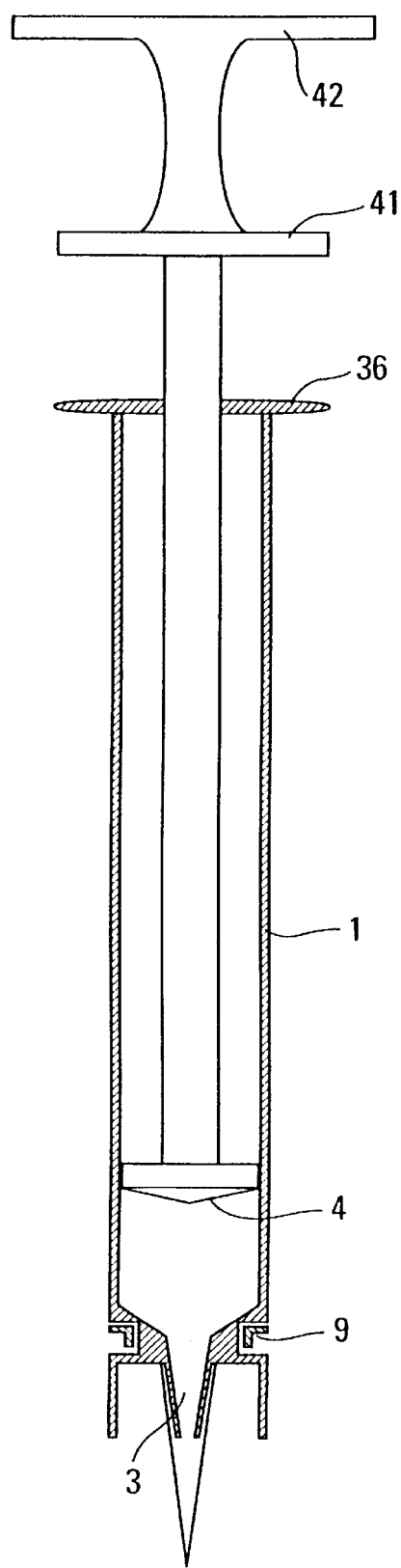
Figure 15:
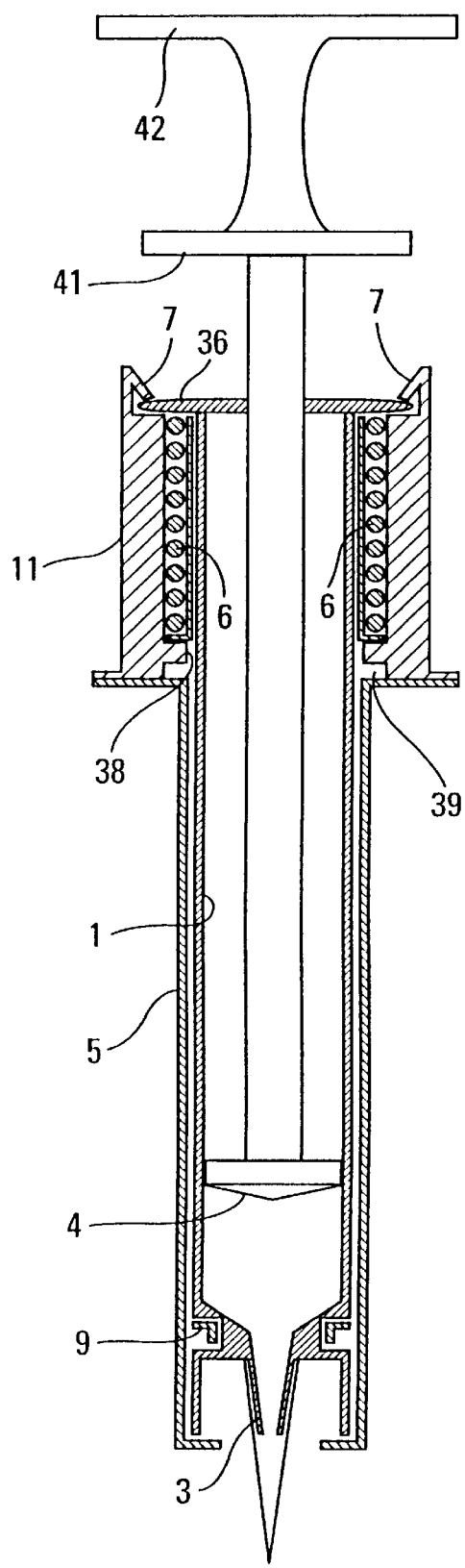

In the appended drawings, which are given by way of non-limiting example:

FIG. 1 is a view in longitudinal section of a syringe in accordance with the invention, FIGS. 2 and 3 are views analogous to FIG. 1 showing how the syringe works, FIG. 4 is a bottom view of a circlip in accordance with the invention, FIG. 5 is a view in section taken along the line V—V in FIG. 4, FIG. 6 is a sectional view of the body of the syringe in accordance with the invention, FIG. 7 is a top view of the part forming the sleeve of the sheath of the syringe in accordance with the invention, FIG. 8 is a view in section taken along the line VII—VII in FIG. 7, FIG. 9 is a view in section taken along the line IX—IX in FIG. 7, FIGS. 10 and 11 are sectional views of other embodiments of a circlip in accordance with the invention, FIGS. 12, 13 and 14 are diagrammatic views illustrating various ways of forming a groove on a syringe body in accordance with the invention, FIG. 15 is a view in longitudinal section of another version of the syringe in accordance with the invention, in a storage configuration, FIG. 16 is a view in section showing only the body and the piston of the syringe from FIG. 15, and FIGS. 17 and 18 are two views analogous to FIG. 15 showing how the syringe works.

Referring first to FIG. 1, the syringe with a self-retracting needle comprises a body 1 carrying injection needle support means 3 at one end 2, a piston 4 mobile in the body 1, a protective sheath 5 inside which the body 1 can slide and a spring 6 disposed between the sheath 5 and the body 1.

The body 1 has an open end and a partly closed end 2.

Integral with the bottom of the end 2 is a needle support 3 having a frustoconical portion serving as a nipple for fixing a conventional needle with a frustoconical fixing termination 19. The frustoconical portion of the needle support 3 has a bore 20 through it through which the interior of the body 1 communicates with the bore in the needle.

A piston 4 sliding freely inside the body 1 can enter the body 1 through the open end of the body 1.

The substantially cylindrical sheath 5 is mounted to slide on the body 1. At one end its wall is reduced in size to form an orifice sufficient for the fixing nipple of the needle to pass through and whose contour can provide a seat for the compression spring 6 whose other end bears on a shoulder at the end 2 of the body 1.

The sheath 5 has a flange 21 at the other end, on which the fingers bear.

The syringe further includes at least one flexible lug 7 carried by the sheath 5 and adapted to cooperate abutment-fashion with a portion 18 of the body 1 to define a first position in which the body 1 is immobilized relative to the sheath in a first direction.

FIG. 1 shows the syringe in this first immobilizing position, corresponding to the storage configuration of the syringe prior to use, in which the spring 6 is compressed and the needle 8 is deployed from the sheath 5.

As shown better in FIG. 6, the portion 18 of the body 1 cooperating with the flexible lugs 7 comprises the frustoconical open end of the body 1, widening towards the open end of the body 1.

The portion 18 could equally be formed by one or more shoulders formed by an additional thickness at the periphery of the body 1.

The flexible lugs 7 are advantageously made in one piece with the sheath, for example from a plastics or other material. Of course, the sheath itself can be made in one piece or as several parts assembled together.

In accordance with the invention, the syringe includes a circlip 9 fitted around the body 1 in a position compressed between the sheath 5 and the body 1 in the first immobilizing position.

In a second immobilizing position, shown in the right-hand part of FIG. 3, the circlip 9 is in a relaxed configuration and has at least one outside contour portion 9a larger than the inside dimension of the sheath 5.

Accordingly, the circlip 9 immobilizes the body 1 in the sheath 5 when it is in this second immobilizing position, in a direction opposite to the first immobilizing direction associated with the flexible lugs 7.

In the second immobilizing position, the spring 6 is at least partially relaxed and the needle 8 is retracted into the sheath 5, the change from the first position to the second position being effected by virtue of cooperation of the piston 4 with the flexible lug(s) 7 to release the lugs 7 from said portion 18 of the body 1 substantially at the end of the travel of the piston 4 and thereby to cause the spring 6 to retract the body 1 into the sheath 5 until it is immobilized in the second position by the circlip 9.

To effect the change from the first immobilizing position to the second immobilizing position, the piston includes a portion 22 which can come into direct contact with the flexible lugs 7, substantially at the end of the injection travel: this portion can be an enlargement of the piston rod or a skirt carried by the piston.

Groove means 10 are adapted to accommodate the circuit 9.

As shown in FIG. 6, in this example the body 1 has two circular shoulders 23 formed on its cylindrical outside wall and defining between them a groove 10 adapted to accommodate the circlip.

Of course, the circular shoulders could be interrupted or replaced by localized lugs for holding the circlip in place around the body 1 in a transverse plane.

The groove means 10 are preferably at the base of the body 1. They can equally well be at any other location on the body 1, including on a skirt 16 extending the body 1 and whose function is described later.

As shown in FIGS. 7, 8 and 9, the sheath 5 has a sleeve part 11 at one end.

The sleeve part 11 can be in one piece with the remainder of the sheath 5 or fixed, for example clipped, around the outside wall of the sheath 5.

In this example, the sleeve part 11 constitutes the end of the sheath, the latter therefore having an elongate part accommodating the body 1 in the first immobilizing position and a sleeve part 11 having an inside diameter greater than that of the elongate part of the sheath 5.

As shown in FIG. 3, the circlip 9 is accommodated inside the sleeve part 11 in the second immobilizing position, with the result that it is protected by the sleeve and is not accessible to the user.

The flexible lug(s) 7 are fixed to the sleeve part 11.

There are four of them in this example and they are arranged in quadrature on the inside wall of the sleeve part 11.

The flexible lugs 7 therefore consist of flexible tongues extending towards the interior of the sleeve part 11.

The lugs 7 form towards the interior of the sheath 5 a unidirectional abutment projection in one direction and a ramp in the other direction.

This facilitates mounting the body 1 in the sheath 5 because the flexible lugs 7 retract against the wall of the sleeve part 11 of the sheath 5 as the portion 18 of the body 1 passes them.

They then resume their projecting position to block the outlet of the body 1.

The sleeve part 11 further includes at least one shoulder 12 adapted to cooperate abutment-fashion with the circlip 9 in the second immobilizing position to immobilize the body 1 in the sheath 5 in said first immobilizing direction.

There are also four of these shoulders 12 in this embodiment, disposed in quadrature on the inside wall of the sleeve part 11, between the flexible lugs 7.

The shoulders 12 are preferably formed of inwardly projecting increased thickness portions of the sleeve part, but projecting a sufficiently small distance from the inside wall of the sleeve part 11 not to impede entry of the body 1 into the sleeve part 11.

The lugs 7 and the shoulders 12 inside the sleeve part 11 can be made in one piece with it, for example moulded in one piece with it.

As shown in FIGS. 4 and 5, the circlip 9 has an L-shaped cross section and the leg 9b of the L-shape is accommodated between the sheath 5 and the body 1 in the second immobilizing position.

In the first immobilizing position, the leg 9b of the L-shape is accommodated in the groove means 10 around the body 1 and the circlip 9 is held compressed by the inside walls of the sheath 5 in contact with the foot 9a of the L-shape of the circlip.

In the second immobilizing position, the leg 9b of the L-shape is held in the groove means 10 and comes into contact with the inside wall of the elongate part of the sheath 5.

The foot 9a of the L-shape of the circlip extends into the sleeve part 11 and prevents reinsertion of the body 1 into the sheath 5. The foot 9a of the L-shape of the circlip would abut against the end of the elongate part of the sheath 5 if the body 1 were to be pushed towards the interior of the sheath 5.

As shown better in FIG. 10, the end 2 of the body 1 carrying the needle support means 3 includes an orifice 13 opening into the needle support means 3.

The orifice 13 connects the body 1 to the bore 20 for feeding the injection needle with the medication.

An end 14 of the piston 4 includes a nipple 15 adapted to be forced into the orifice 13, substantially at the end of the travel of the piston 4.

The orifice 13 is therefore blocked by the nipple 13 and the piston 4 remains fastened to the bottom of the body 1.

The nipple 15 is preferably fixed to the end 14 of the piston 4 through a thinner area so that if the user attempts to withdraw the piston 4 from the body 1 the nipple 15 remains trapped in the orifice 13 and is detached from the end 14 of the piston 4.

The bore 20 is then also blocked by the nipple 15, preventing use of the syringe for a new injection.

In this example, the nipple 15 is formed of two truncated cones joined together at their base and the orifice 13 has a complementary shape.

The end 2 of the body 1 further includes two annular skirts 16, 17 extending around the injection needle support means 3 and defining an annular housing to receive the spring 6.

How the syringe works will now be described with reference to FIGS. 1, 2 and 3.

In the storage configuration shown in FIG. 1, corresponding to arming of the syringe, the flexible lugs 7 cooperate with the body 1 to immobilize the body 1 in the sheath 5 with the spring 6 compressed. The same lugs 7 can be spread apart by the skirt 22 when the piston 4 is pressed into the body 1. The spring 6 then expands and pushes the sheath 5 out of the body 1 into the second immobilizing position (shown in FIG. 3) in which the shoulders 12 cooperate with the circlip 9.

The shoulders 12 and the circlip therefore prevent the body 1 and its needle 8 from being withdrawn from the sheath 5 which then covers the needle.

The circlip 9 also prevents the needle 8 from being deployed out of the sheath again. In this way, after the injection, the body 1 remains immobilized, both at the front and at the rear, in the position shown in the right-hand part of FIG. 3, and the needle 8 is inaccessible.

Moreover, the piston 4 remains immobilized at the bottom of the body 1 when it reaches the end of its travel, because the nipple 15 is retained in the orifice 13 at the end 2 of the body 1.

Of course, the invention is not limited to the example described above to which many modifications can be made without departing from the scope of the invention.

In FIG. 5, the semi-annular immobilizing circlip with an L-shaped cross section has a foot 9a constituting the part of the circlip 9 cooperating with a shoulder of the sheath to prevent reinsertion of the body 1 into the sheath and to prevent sliding of the body 1 in the sheath.

As shown in FIGS. 10 and 11, the size of the leg 9b and the foot 9a of the L-shaped circlip can vary. Accordingly, in FIG. 10, the foot 9'a and the leg 9'b of the circlip have the same length and thickness.

In FIG. 11, the foot 9"a of the circlip is thinner than the leg 9"b of the circlip 9", differing in this respect from the circlip shown in FIG. 5.

Moreover, FIGS. 12 to 14 show various ways of forming the groove 10 on the body 1 of the syringe.

Accordingly, instead of forming the groove 10 by adding circular shoulders 23 forming abutments molded onto the body 1, as shown in FIG. 6, an independent device 25, 25' or 25" can be fixed to the body 1 of the syringe.

A device of this kind can be used on glass syringes, possibly of the pre-filled type, or even conventional plastics material syringes.

In FIG. 12, the device 25 is formed of a ring with a substantially U-shaped cross section which forms the groove 10. The ring can comprise two half-rings joined by a hinge 26. It is then sufficient to pivot the half-rings at the hinge 26 to close the ring 25 onto the body 1 of the syringe. The ring 25 may be glued or welded to the body 1.

In accordance with another principle shown in FIG. 13, the device 25' can have a substantially cylindrical shape with a groove 10 at its perimeter similar to that shown in FIG. 12.

The device 25' includes two half-cylinders which can pivot on a hinge 26 so that they can be closed around the body 1 of a syringe, as in the device shown in FIG. 12.

Furthermore, the cylinder 25' has at one end an annular groove 27 open towards the interior of the cylinder 25' and adapted to espouse a complementary circular shape of the syringe body in order to fix the device 25' to the body 1 and to prevent it sliding in the longitudinal direction of the body.

Similarly, in FIG. 14, a device 25" includes a ring with a groove 10 similar to that shown in FIG. 12 and extended by a substantially frustoconical sleeve 28 adapted to be forced over the end of the body 1 of the syringe carrying the injection needle.

This end of the syringe body can include an excrescence 29 adapted to prevent movement in translation of the device 25" once it has been mounted on the syringe body.

The devices 25, 25' and 25" therefore constitute a simple way of providing a groove 10 adapted to accommodate an immobilizing circlip 9 on the body 1 of a conventional syringe.

Like that shown in FIGS. 1 to 3, the syringe shown in FIGS. 15 to 18 comprises a body 1 carrying injection needle support means 3 at one end, a piston 4 mobile inside the body 1 and a protective sheath 5 inside which the body 1 can slide.

At the end opposite the needle, the sheath 5 carries a sleeve 11 whose diameter is larger than that of the sheath 5.

The free end of the sleeve 11 carries lugs 7 which, in a storage configuration of the syringe (see FIG. 15), immobilize the flange 36 carried by the adjacent end of the body 1 relative to the sleeve 11.

The embodiment shown in FIGS. 15 to 18 differs from that shown in FIGS. 1 to 3 primarily by the disposition of the compression spring 6 between the sleeve 11 and the portion of the body 1 adjacent its end flange 36.

Respective opposite ends of the spring 6 bear against the flange 36 of the body and an inside shoulder 38 of the sleeve 11 projecting towards the body 1.

A circlip 9 engaged over the end of the body 1 adjacent the needle elastically relaxes in a groove 39 between the shoulder 38 on the sleeve 11 and the adjacent end of the sheath 5, in said second position of immobilization, to immobilize the body 1 relative to the sheath 5 after the body moves outwards as far as the position shown in FIG. 18.

The syringe shown in FIGS. 15 to 18 works as follows:

In the storage configuration, as shown in FIG. 15, the elastic lugs 7 immobilize the body 1 relative to the sheath 5 and the spring 6 is in a compressed configuration.

The elastic lugs 7 are pushed outwards (see FIG. 17) by the flange 41 provided under the button 42 of the piston 4 when the piston is pressed into the body 1.

The flange 36 of the body 1 is therefore released from the sleeve 11 and the spring 6 can then expand to move the body 1 relative to the sheath 5 until the circlip 9 engages in the groove 39, as shown in FIG. 18.

In this position, the body 1 cannot be withdrawn from the sheath 5 and the needle is entirely contained within the sheath 5.

Similarly, in the position shown in FIG. 18, it is not possible to move the body 1 to deploy the needle out of the sheath 5 again.

What is claimed is:

1. Syringe with a self-retracting needle, comprising a body (1) carrying at one end (2) injection needle support means (3), a piston (4) mobile in said body (1), a sheath (5) in which said body (1) can slide, a spring (6) disposed between the sheath (5) and the body (1), at least one flexible lug (7) cooperating abutment-fashion with a portion (18) of said body (1) to define a first position of immobilization of the body (1) relative to the sheath (5) in a first direction, the spring (6) being compressed and the needle (8) deployed from the sheath (5) in this first position, and immobilizing means for immobilizing the body (1) in the sheath (5) in a second immobilizing position, the spring (6) being at least partially relaxed and the needle (8) being inside the sheath (5) in this second position, the change from the first position to the second position being effected by cooperation of the piston (4) with said flexible lug (7) to release the lug (7) from said portion (18) of the body (1) substantially at the end of the travel of the piston (4) and thereby to cause the spring (6) to retract the body (1) into the sheath (5) until it is immobilized in the second position, characterized in that the immobilizing means comprise a circlip (9) mounted around said body (1) in a compressed configuration between the sleeve (5) and the body (1) in said first immobilizing position and in a relaxed configuration in said second immobilizing position, the sheath (5) having at one end a sleeve part (11), the circlip (9) having at least one part (9a) housed inside the sleeve part (11) in said second immobilizing position between said end of the sheath and at least one shoulder (12) of the sleeve part (11) adapted to cooperate abutment-fashion with the circlip (9) in said second immobilizing position to immobilize the body (1) in the sheath (5) in said first direction.

2. Syringe according to claim 1, characterized in that the circlip (9) has an L-shaped cross section, the leg (9b) of the L-shape being accommodated between the sheath (5) and the body (1) in said second immobilizing position.

3. Syringe according to claim 1, characterized in that said body (1) comprises groove means (10) adapted to accommodate said circlip (9).

4. Syringe according to claim 1, characterized in that said flexible lug (7) is fixed to the sleeve part (11).

5. Syringe according to claim 1, characterized in that the end (2) of the body (1) carrying the needle support means (3) includes an orifice (13) opening into the needle support means (3), one end (14) of the piston (4) including a nipple (15) adapted to be forced into said orifice (13).

6. Syringe according to claim 5, characterized in that said nipple (15) is fixed to the end (14) of the piston (4) by a thinner area (15a).

7. Syringe according to claim 1, characterized in that the circlip is semi-annular in shape with an L-shape cross section, the foot (9a) of the L-shape constituting said part (9a) adapted to cooperate with a shoulder of the sleeve part (11) to prevent the body (1) from sliding in said sheath (5).

8. Syringe according to claim 1, characterized in that said sleeve (11) of the sheath has a diameter which is enlarged relative to that of the sheath (5), the free end of the sleeve (11) carrying lugs (7) which immobilize a part (36) carried by the body when the syringe is in the storage configuration.

9. Syringe according to claim 8, characterized in that said spring (6) is disposed between the sleeve (11) and the body (1), the spring (6) being compressed between the part (36) of the body (1) and a shoulder (38) inside the sleeve (11).

10. Syringe according to claim 8, characterized in that the sleeve (11) incorporates a groove (39) in which a circlip (9) engaged on the end of the body (1) adjacent the needle elastically relaxes to immobilize the body (1) in said second position of immobilization after movement thereof towards the outside of the sheath (5).

* * * * *